United States Patent
Lee, Jr. et al.

(10) Patent No.: US 12,303,452 B2
(45) Date of Patent: May 20, 2025

(54) SYSTEMS AND METHODS FOR LASER TREATMENT OF CELLULITE

(71) Applicants: John B. Lee, Jr., Ridgefield, CT (US); William James Lee, Ridgefield, CT (US)

(72) Inventors: John B. Lee, Jr., Ridgefield, CT (US); William James Lee, Ridgefield, CT (US)

(73) Assignee: CarbonWave, Inc., Bethel, CT (US)

( * ) Notice: Subject to any disclaimer, the term of this patent is extended or adjusted under 35 U.S.C. 154(b) by 299 days.

(21) Appl. No.: 17/825,234

(22) Filed: May 26, 2022

(65) Prior Publication Data

US 2022/0387251 A1    Dec. 8, 2022

Related U.S. Application Data (60) Provisional application No. 63/197,034, filed on Jun. 4, 2021.

(51) Int. Cl.
*A61N 5/067* (2006.01)
*A61H 23/00* (2006.01)
(Continued)

(52) U.S. Cl.
CPC .......... *A61H 23/008* (2013.01); *A61L 31/024* (2013.01); *A61L 31/145* (2013.01);
(Continued)

(58) Field of Classification Search
CPC .............. A61H 23/008; A61H 2201/10; A61H 2207/00; A61H 2201/1654; A61H 2201/5005; A61L 31/024; A61L 31/145; A61N 5/0616; A61N 5/067; A61B 2017/0019; A61B 2018/00702;
(Continued)

(56) References Cited

U.S. PATENT DOCUMENTS 6,050,990 A     4/2000   Tankovich et al.
6,306,128 B1 *  10/2001  Waldman ............. A61B 18/203
                                                  606/9
(Continued)

FOREIGN PATENT DOCUMENTS

WO    2021/0466360 A1    3/2021

OTHER PUBLICATIONS

"PCT Notification of Transmittal of the International Search Report and the Written Opinion", of the International Searching Authority, or The Declaration, dated Nov. 7, 2022 (Jul. 11, 2022), for International Application No. PCT/US2022/031254, 12pgs.

*Primary Examiner* — Scott M. Getzow
(74) *Attorney, Agent, or Firm* — Buckley, Maschoff & Talwalkar LLC (57) ABSTRACT

Some embodiments are directed to a cellulite treatment system that contains a laser generating device. A hydrogel patch may include a region, at a first side of the hydrogel patch, to be in contact with a person's skin. The region may contain an adsorbing medium (e.g., carbon black or any other substance that would have a similar effect) that, when receiving a laser beam from the laser generating device, results in Extracorporeal Shock Wave Therapy ("ESWT") being applied to the person's skin to treat cellulite.

6 Claims, 9 Drawing Sheets

(51) Int. Cl.
  *A61L 31/02*  (2006.01)
  *A61L 31/14*  (2006.01)
  *A61N 5/06*  (2006.01)
  *A61B 17/00*  (2006.01)
  *A61B 18/00*  (2006.01)

(52) U.S. Cl.
  CPC ........... *A61N 5/0616* (2013.01); *A61N 5/067* (2021.08); *A61B 2017/0019* (2013.01); *A61B 2018/00702* (2013.01); *A61H 2201/10* (2013.01); *A61H 2207/00* (2013.01)

(58) Field of Classification Search
  CPC .... A61B 2018/00452; A61B 2018/263; A61B 18/26; A61B 18/203; A61B 2018/00464
  See application file for complete search history.

(56) References Cited

U.S. PATENT DOCUMENTS

| | | |
|---|---|---|
| 2014/0243715 A1 | 8/2014 | Cioanta et al. |
| 2016/0016013 A1 | 1/2016 | Capelli et al. |
| 2021/0052292 A1* | 2/2021 | Karni .................... A61B 18/26 |

* cited by examiner

SYSTEMS AND METHODS FOR LASER TREATMENT OF CELLULITE

CROSS-REFERENCE TO RELATED APPLICATION

The present application claims the benefit of U.S. Provisional Patent Application No. 63/197,034 entitled "LASER TREATMENT OF CELLULITE" and filed on Jun. 4, 2021. The entire content of that application is incorporated herein by reference.

BACKGROUND

In some cases, a herniation of subcutaneous fat within fibrous connective tissue may manifest as skin dimpling and nodularity in certain areas of a person's skin. This condition, referred to as "cellulite," may result from hormonal factors, genetic factors, pre-disposing factors, lifestyle, etc. Many treatments have been developed for cellulite, including non-invasive therapy (mechanical suction or mechanical massage), energy-based devices (radio frequency with deep penetration of the skin, ultrasound, laser, and pulsed-light devices). More invasive subcision techniques may utilize a needle-sized microscalpel to cut through causative fibrous bands of connective tissue. Subcision procedures (manual, vacuum-assisted, or laser-assisted) are usually performed in specialist clinics. All existing treatments, however, suffer from drawbacks and disadvantages.

It would therefore be desirable to provide systems and methods that treat cellulite with a laser in a new and improved approach.

SUMMARY

Some embodiments are directed to a cellulite treatment system that contains a laser generating device. A hydrogel patch may include a region, at a first side of the hydrogel patch to be in contact with a person's skin. The region may contain an adsorbing medium that, when receiving a laser beam from the laser generating device, results in Extracorporeal Shock Wave Therapy ("ESWT") being applied to the person's skin to treat cellulite.

Some embodiments comprise: means for means for placing a first side of a hydrogel patch on a person's skin, the first side including an adsorbing medium; means for generating a laser beam by a laser generating device; and means for directing the laser beam to apply Extracorporeal Shock Wave Therapy ("ESWT") to the person's skin to treat cellulite.

Some technical advantages of embodiments disclosed herein are improved systems and methods to facilitate the treatment of cellulite with a laser in a new and improved approach.

DETAILED DESCRIPTION

In the following detailed description, numerous specific details are set forth in order to provide a thorough understanding of embodiments. However, it will be understood by those of ordinary skill in the art that the embodiments may be practiced without these specific details. In other instances, well-known methods, procedures, components, and circuits have not been described in detail so as not to obscure the embodiments.

Figure 1:
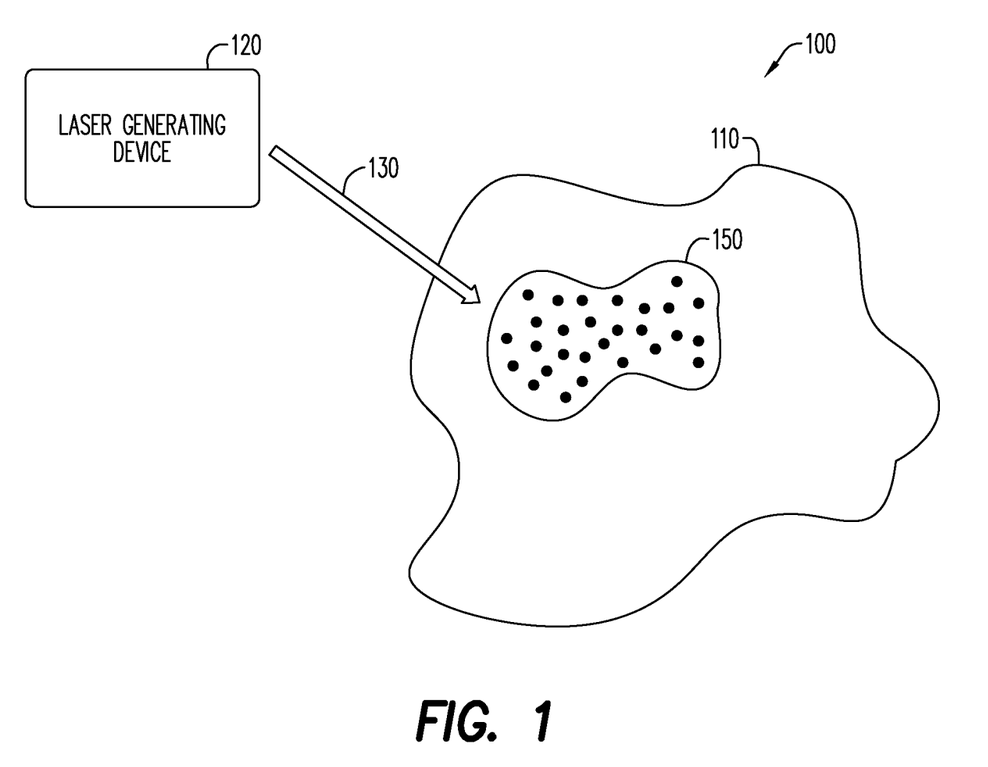
FIG. 1 is a high-level block diagram of a laser cellulite treatment system in accordance with some embodiments.

FIG. 1 is a high-level block diagram of a laser cellulite treatment system 100 in accordance with some embodiments. According to some embodiments, the system 100 may treat a person's skin 110 using Extracorporeal Shock Wave Therapy ("ESWT"). As used herein, ESWT may refer to a non-invasive procedure that sends powerful acoustic shock waves or pulses into soft tissue. In particular, a laser generating device 120 may direct a laser beam 130 to an adsorbing medium 150 adjacent to a person's skin 110. As used herein, the terms "adsorption" and "adsorbing" may refer to an adhesion of atoms, ions, or molecules from a gas, liquid, or dissolved solid to a surface. The process may create a film of the adsorbate on the surface of the adsorbent. Adsorption is present in many natural, physical, biological, and chemical systems and is used in many industrial applications such as heterogeneous catalysts, activated charcoal, synthetic resins, etc. In some embodiments, the adsorbing medium 150 is carbon lotion that creates an acoustic explosion strong enough to treat fascia in legs (e.g., to treat cellulite).

The adsorbing medium 150 may be a strong adsorber of the laser energy and may need to be spread on the surface of the skin 110. The laser pulse may be absorbed quickly creating an explosive response that creates a shock wave. An optically clear material covering the adsorbing medium 150 (such that the laser beam 130 can pass through) may be used to contain the shock wave and direct it into the skin 110. The adsorbing medium 150 might be carbon black. As used herein, the phrase "carbon black" (including acetylene black, channel black, furnace black, lamp black, thermal black, etc.) may refer to a material produced by the incomplete combustion of heavy petroleum products (e.g., fluid catalytic cracking tar, coal tar, ethylene cracking tar, vegetable matter, etc.). Carbon black is a form of paracrystalline carbon that has a high surface-area-to-volume ratio (although lower than that of activated carbon). The adsorbing medium 150 could be suspended in mineral oil or in a coating material that can be applied to the person's skin 110. According to some embodiments, the treatment may be done without a hydrogel patch or with a different optically clear material that can contain the carbon black (or any other substances that would have a similar effect). A simple plastic wrap or silicone patch might be used. Note that the absorber and the laser may need to be matched. Moreover, carbon black may comprise a good absorber for many wavelengths.

The laser is preferably absorbed quickly enough to create a shock wave (usually this means a plasma is formed when the absorber is irradiated by the laser). Some embodiments may use paper with black ink specifically formulated to be absorbed (e.g., ZAP-IT® laser alignment and burn paper could generate the shock wave).

In this way, some embodiments may provide a carbon patch accessory device that will work with many commercially available nanosecond lasers (e.g., Q-Switched lasers typically used for tattoo removal). The patch may be affordable, easy to train, non-invasive, and effective. Some embodiments may utilize a fourth generation Q-Switched laser, such as one capable of delivering laser energy at 50 Hz, with 30 Watt 1064 nm laser energy. As used herein, the phrase "Q-Switched laser" may refer to a technique by which a laser can be made to produce a pulsed output beam. The technique allows the production of light pulses with substantially high (e.g., gigawatt) peak power (higher than would be produced by the same laser if it were operating in a continuous wave or constant output mode). Compared to mode locking (another technique for pulse generation with lasers) Q-switching can lead to substantially lower pulse repetition rates, higher pulse energies, and longer pulse durations.

Figure 2:
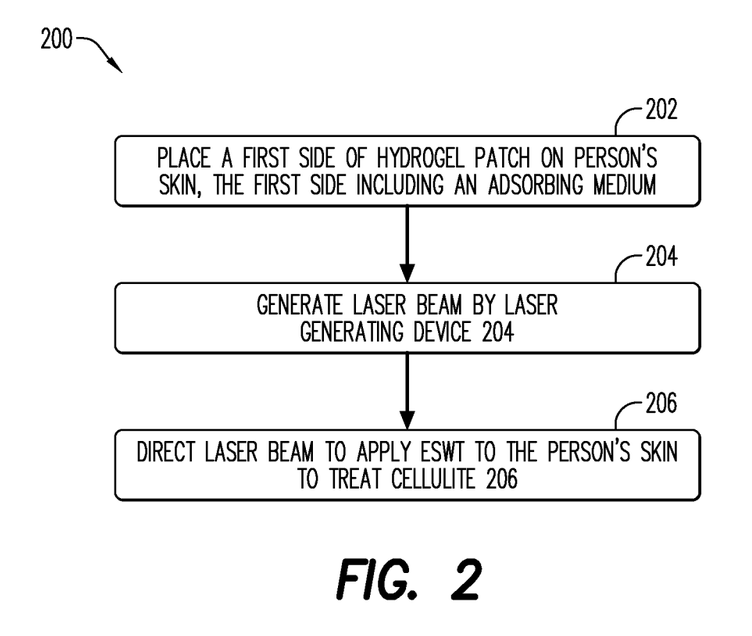
FIG. 2 is a laser cellulite treatment method according to some embodiments.

FIG. 2 is a laser cellulite treatment method 200 according to some embodiments. At 202, the system may place a first side of a hydrogel patch on a person's skin, the first side including an adsorbing medium. At 204, a laser beam may be generated by a laser generating device. At 206, the laser beam may be directed to apply ESWT to the person's skin to treat cellulite.

Figure 3:
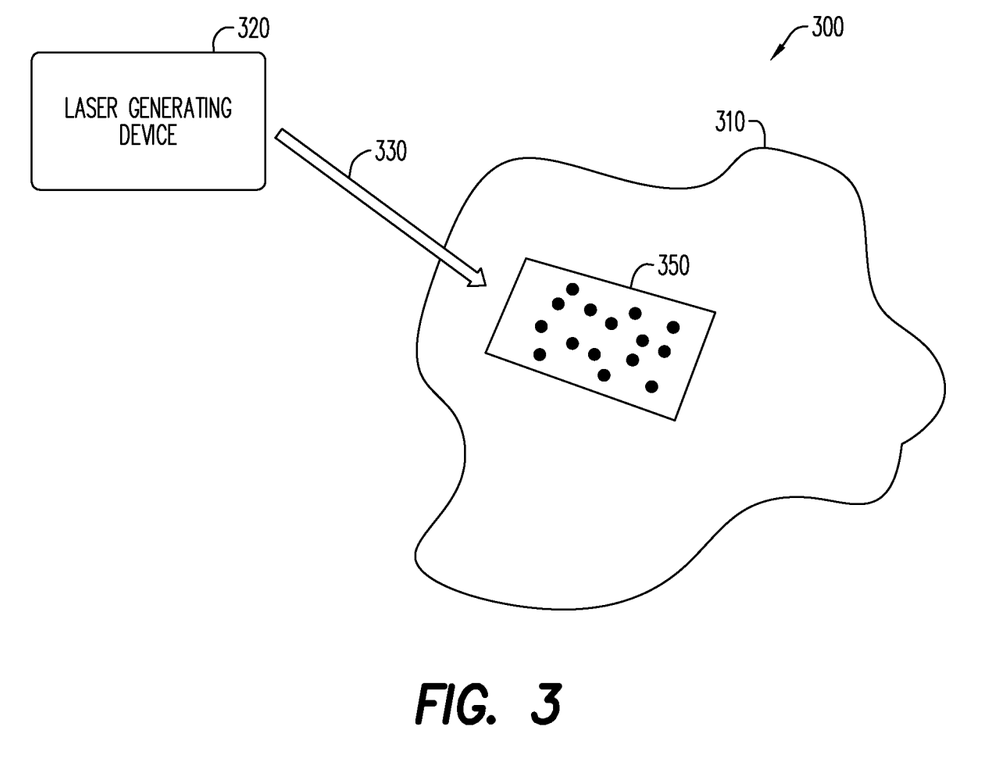
FIG. 3 is a laser cellulite treatment system in accordance with some embodiments.
Figure 4:
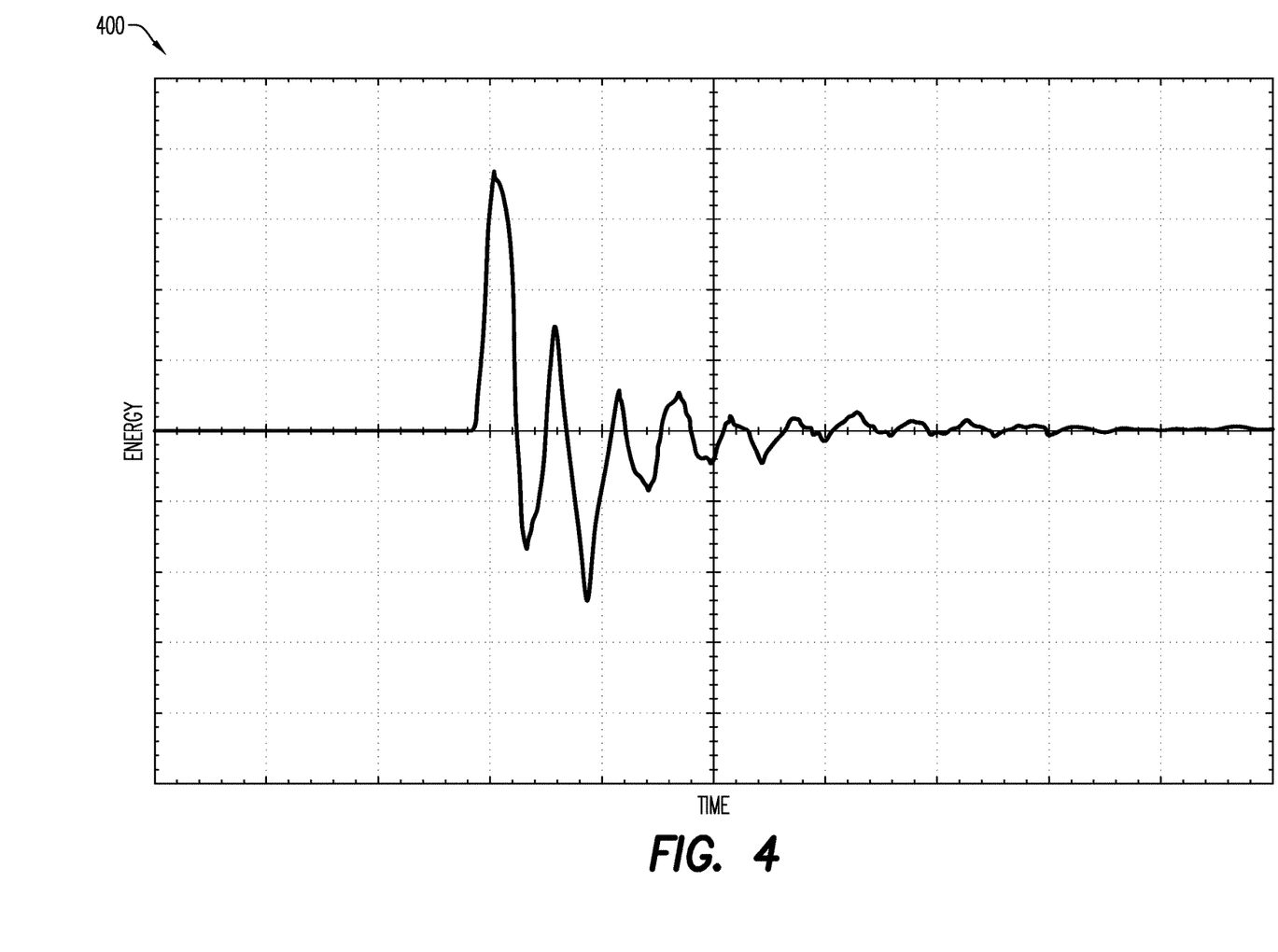
FIG. 4 illustrates acoustic wave energy created by laser reaction with a carbon patch according to some embodiments.

FIG. 3 is a laser cellulite treatment system 300 in accordance with some embodiments. As before, a laser generating device 320 directs a laser beam 330 to an adsorbing medium adjacent to the person's skin 310. In this embodiment, the adsorbing medium is a hydrogel or similar patch 350 that creates an ESWT acoustic explosion strong enough to treat cellulite. As used herein, the term "hydrogel" may refer to a material with a three-dimensional network of hydrophilic polymers that can swell in water (and hold a substantial amount of water) while maintaining the structure due to chemical or physical cross-linking of individual polymer chains. The hydrogel patch 350 can be precoated with the adsorbing medium. This makes application of the adsorber easier and enhances the treatment by helping to direct the shock wave into the skin 310. According to some embodiments, the hydrogel patch 350 is an approximately 8" by 4" gel sheet (with a layer of carbon black—or any other substances that would have a similar effect—between gel layers) that might be applied to a person's legs, buttocks, abdominal region, arms, etc. Different shapes and sizes of the patch 350 may be used for specific treatment areas. The laser generating device 320 results in an explosion of carbon particles that creates an acoustic sound wave that penetrates deep into tissue. FIG. 4 illustrates 400 ESWT acoustic wave energy created by laser reaction with a carbon patch (with the X-axis representing time and the Y-axis representing energy). Note that encapsulating the carbon in gel sheets may help direct energy into the person's skin 310.

Figure 5:
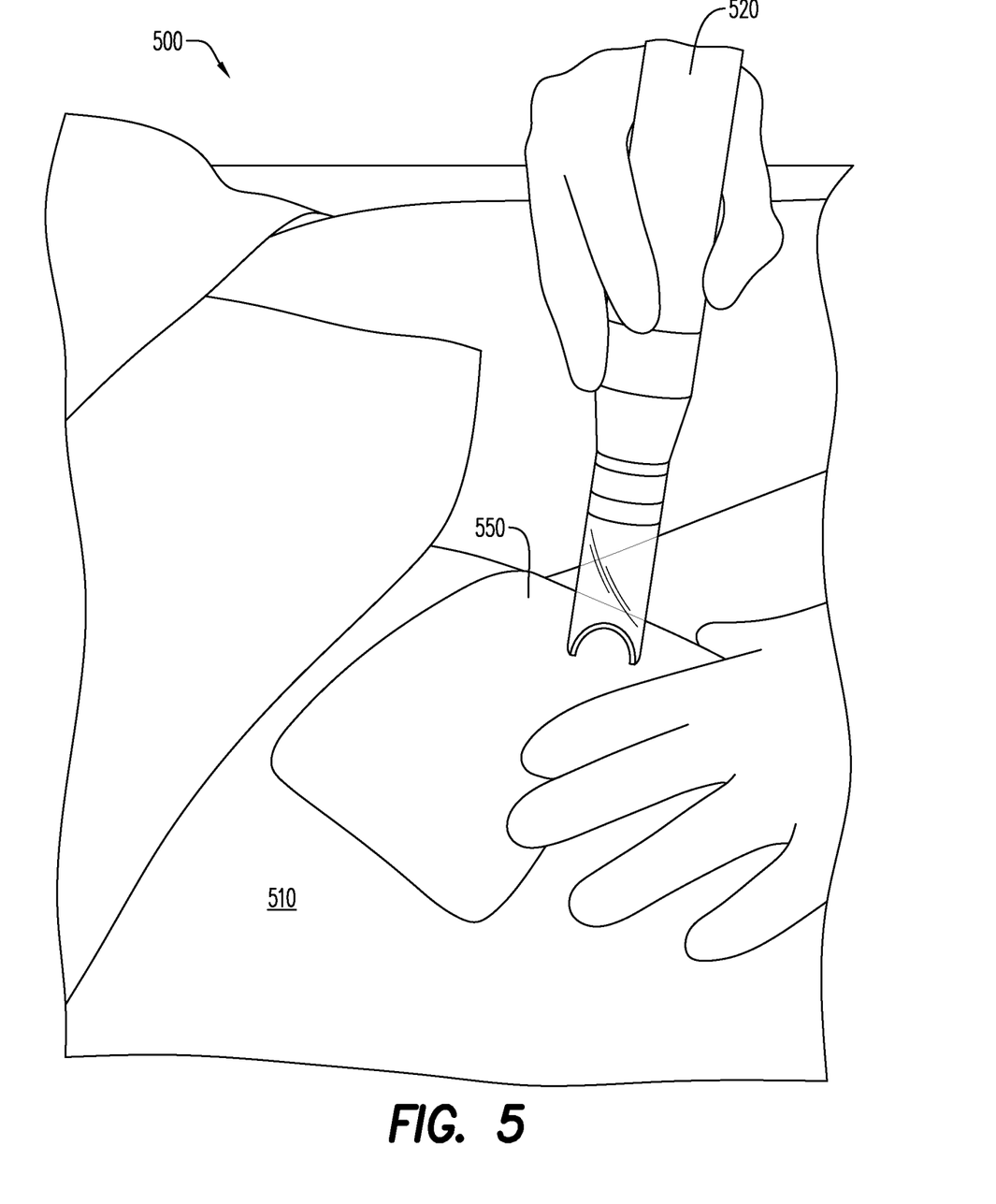
FIG. 5 illustrates a patch on a person's being receive laser energy from a scanner in accordance with some embodiments.

According to some embodiments, the laser generating device 320 utilizes a 50 Hz pulse rate. The 50 Hz pulse rate may deliver more energy as compared to typical lasers, resulting in the creation of higher pressure acoustic pulses. Note that the pulse rate might, according to some embodiments, be adjusted to generate a resonance of shock waves that corresponds to a natural resonance of target tissue. In some cases, the 50 Hz pulse rate may be too fast for a typical laser handpiece. Instead, a custom designed scanner may be used. In this case, each 8" by 4" hydrogel patch 350 may take approximately one to two minutes of treatment time. FIG. 5 illustrates 500 a patch 550 on a person's leg 510 receiving laser energy from a scanner 520 in accordance with some embodiments.

Thus, embodiments may create an acoustic wave of energy, by using a laser interaction with carbon particles, for the treatment of cellulite. The hydrogel patch 350 is infused with carbon particles. A doctor or technician creates an acoustic wave by lasering the hydrogel patch 350. When the laser beam 330 reacts with carbon particles, it creates an acoustic wave. Acoustic waves have been studied and proven to be successful in the treatment of cellulite.

The laser generating device 320 might be associated with, according to some embodiments, lasers having a wavelength from 755 to 1064 nanometers ("nm"). The laser beam 330 may have a pulse width from 0.2 to 80 nanoseconds ("ns") and pulse energy might range from 100 to 2500 millijoules ("mj"). The laser beam 330 may have a spot size of from 1 to 15 millimeters and a fluence of 0.1 to 5 j/cm$^2$. According to some embodiments, a larger spot size (e.g., 100 or larger) may generate a deeper penetrating shock wave. One example of a suitable laser generating device 320 might comprise a Q-Switched ND:YAG (1064 nm, pulse energy 400-2000 mj, spot size 4-12 mm, fluence 0.7 to 2.5 j/cm$^2$, and pulse width 3-12 ns). Other suitable laser generating devices 320 might be associated with wavelengths from 690 to 1200 nm, pulse widths from 0.1 ns to 1 ms, spot sizes from 1 to 15 mm, scanning areas up to 40×40 mm, fluence 0.1 to 5 j/cm$^2$, and pulse energy from 100 to 4000 mj.

Figure 6A:
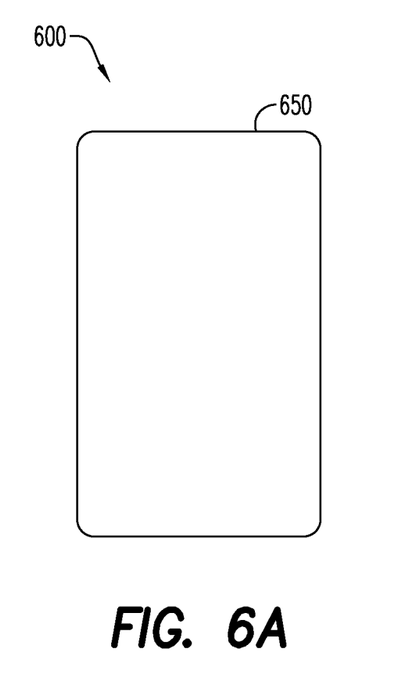
FIGS. 6A, 6B, and 6C illustrate views of a hydrogel patch according to some embodiments.
Figure 6B:
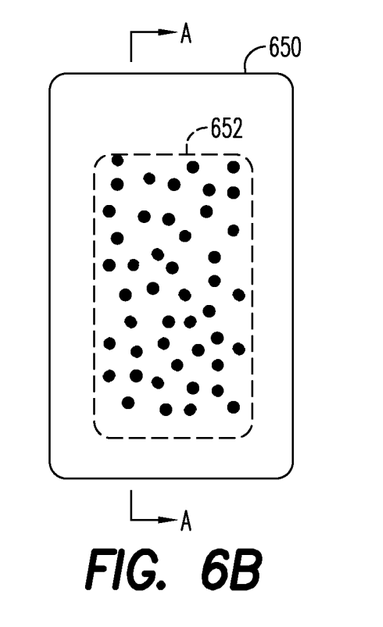
Figure 6C:
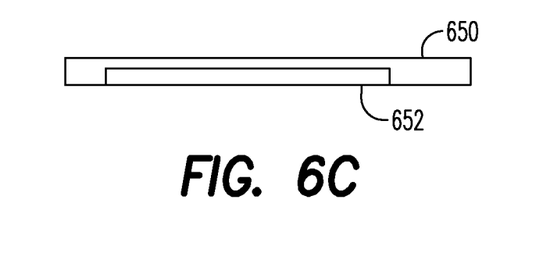

FIGS. 6A, 6B, and 6C illustrate views of a hydrogel patch 650 according to some embodiments. In particular, FIG. 6A is view 600 of the top of the hydrogel patch 650 and FIG. 6B is a view of the bottom of the hydrogel patch 650 (the side applied to a person's skin). As can be seen, a portion 652 of the bottom side has been infused with carbon particles. FIG. 6C is a cross-sectional side view of the hydrogel patch 650 taken along cross section line AA of FIG. 6B. The carbon particle infused portion 652 of the patch 650 would therefore be placed directly up against a person's skin in an area to be treated for cellulite.

Figure 7A:
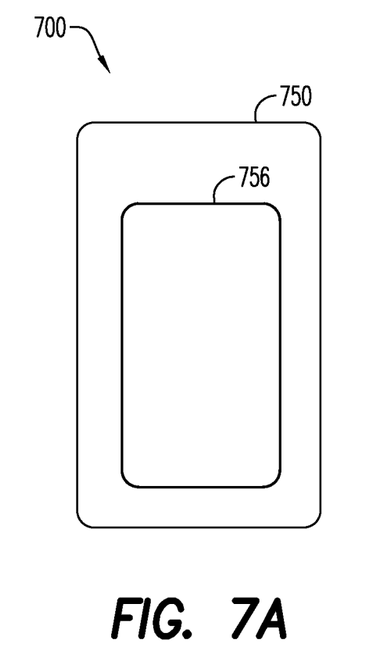
FIGS. 7A, 7B, and 7C illustrate views of a hydrogel patch according to another embodiment.
Figure 7B:
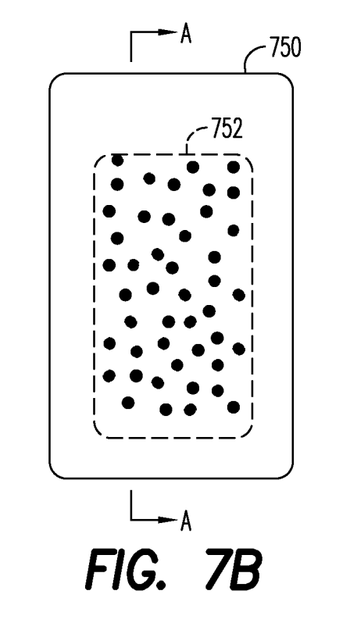
Figure 7C:
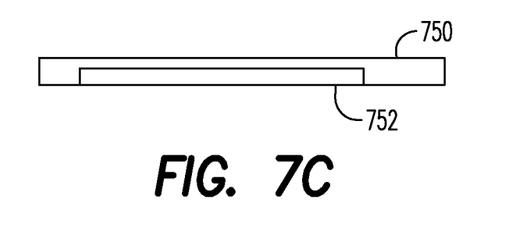

FIGS. 7A, 7B, and 7C illustrate views of a hydrogel patch 750 according to another embodiment. As before, FIG. 7A is view 700 of the top of the hydrogel patch 750 and FIG. 7B is a view of the bottom of the hydrogel patch 750 (the side applied to a person's skin). As can be seen, a portion 752 of the bottom side has been infused with carbon particles. FIG. 7C is a cross-sectional side view of the hydrogel patch 750 taken along cross section line AA of FIG. 7B. The carbon particle infused portion 752 of the patch 750 would therefore be placed directly up against a person's skin in an area to be treated for cellulite. Note that the entire surface of the hydrogel patch 750 does not contain the infused portion 752. As a result, markings 756 on the top of the hydrogel patch 750 may help guide a doctor or other professional to exactly where the laser beam should be focused.

Figure 8A:
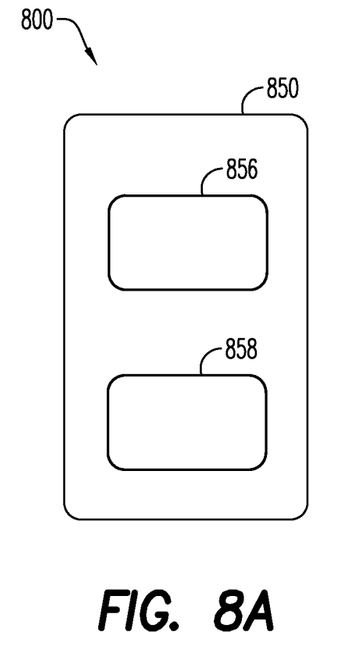
FIGS. 8A, 8B, and 8C illustrate views of a hydrogel patch in accordance with some embodiments.
Figure 8B:
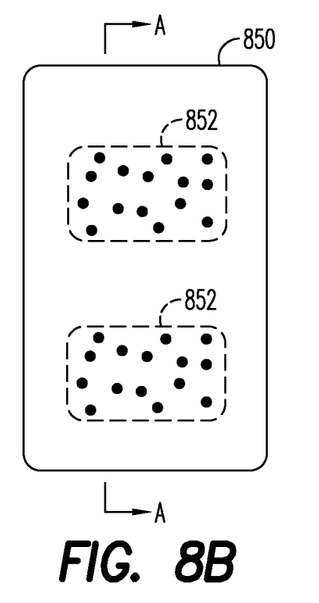
Figure 8C:
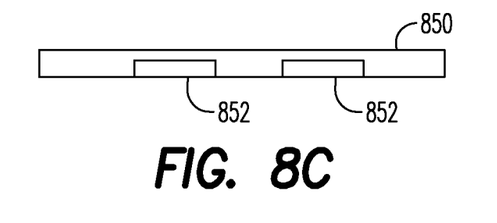

Similarly, FIGS. 8A, 8B, and 8C illustrate views of a hydrogel patch 850 in accordance with some embodiments. Again, FIG. 8A is view 800 of the top of the hydrogel patch 850 and FIG. 8B is a view of the bottom of the hydrogel patch 850 (the side applied to a person's skin). As can be seen, two separate portions 852 of the bottom side has been infused with carbon particles. FIG. 8C is a cross-sectional side view of the hydrogel patch 850 taken along cross section line AA of FIG. 8B. The two carbon particle infused portions 852 of the patch 850 would therefore be placed directly up against a person's skin in an area to be treated for cellulite. Note that the once again, the entire surface of the hydrogel patch 850 does not contain the two infused portions 852. As a result, multiple markings 856, 858 on the top of the hydrogel patch 850 may help guide a doctor or other professional to where the laser beam should be focused.

Figure 9A:
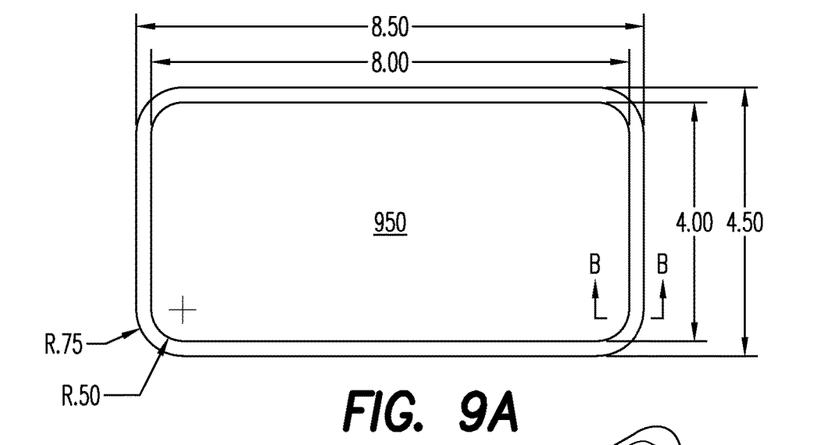
FIGS. 9A, 9B, and 9C illustrate views of a carbon patch according to some embodiments.
Figure 9B:
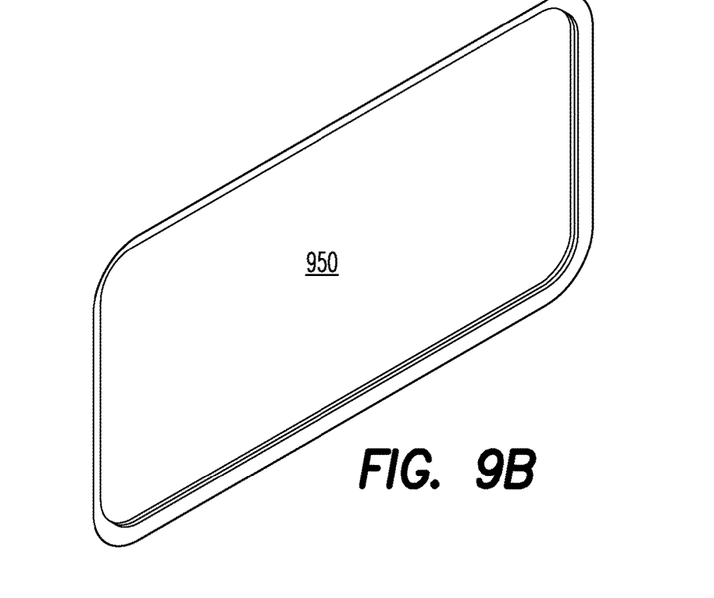
Figure 9C:
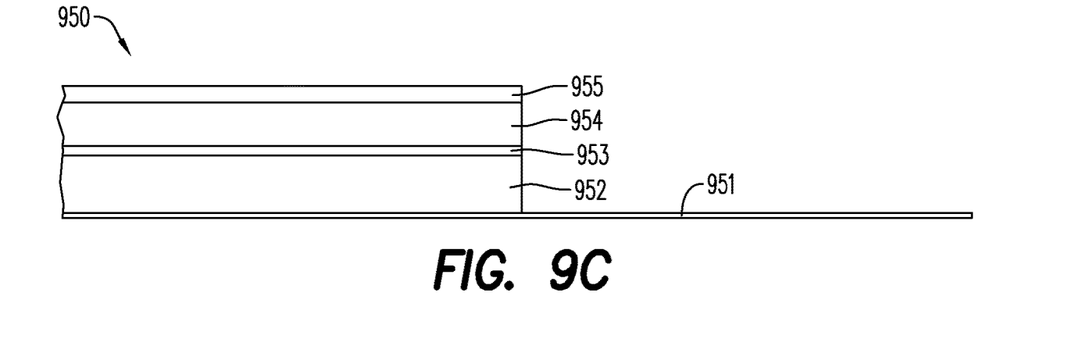

FIGS. 9A, 9B, and 9C illustrate views of a carbon patch 950 according to some embodiments (distances in inches). In particular, FIG. 9A is view of the top of the carbon patch 950 and FIG. 9B is a perspective view of the carbon patch 950. FIG. 9C is a side view illustrating layers of the carbon patch 950. A first layer 951 may represent a release layer and may comprise a 5.5 millimeter clear evape film material. A second layer 952 may represent a hydrogel 1 layer and may comprise a 32 millimeter KM40C hydrogel material available from KATECHO®. A third layer 953 may represent a carbon layer and may comprise a ITW thermal films W90/B220 (e.g., a resin enhanced wax Thermal Transfer Ribbon ("TTR")) available from SHINEMARK® or an equivalent material. A fourth layer 954 may represent a hydrogel 2 layer and may comprise a 32 millimeter KM40C hydrogel material (e.g., similar to the second layer 952). According to some embodiments, the second layer 952 may be thinner than the fourth layer 954 to improve performance. In still other embodiments, the fourth layer 954 may be eliminated entirely (that is, the fourth layer 954 may be optional). A fifth layer 955 may represent a cover layer and may comprise a 3 millimeter clear polyester ("PET") release liner material.

Thus, embodiments may provide fully body rejuvenation. Moreover, some embodiments may target superficial and deeper skin structures. The present invention has been described in terms of several embodiments solely for the purpose of illustration. Persons skilled in the art will recognize from this description that the invention is not limited to the embodiments described but may be practiced with modifications and alterations limited only by the spirit and scope of the appended claims.

The invention claimed is:

1. A cellulite treatment system, comprising:
    a laser generating device including a scanner to provide 50 Hz Q-Switched laser energy, and
    a hydrogel patch to be in contact with a person's skin, including:
        a first layer comprising a 5.5 millimeter thick clear evape film material,
        a second layer comprising a 32 millimeter thick hydrogel material,
        a third layer comprising a resin enhanced wax Thermal Transfer Ribbon ("TTR") with a carbon black adsorbing medium that, when receiving a laser beam from the laser generating device, results in Extracorporeal Shock Wave Therapy ("ESWT") being applied to the person's skin to treat cellulite,
        a fourth layer comprising a hydrogel material,
        a fifth layer comprising a 3 millimeter clear polyester ("PET") release liner material, and
        a plurality of markings on the hydrogel patch to help guide a doctor or other professional to multiple areas where the laser beam should be focused.

2. The system of claim 1, wherein the laser beam has a pulse width from 2 to 80 nanoseconds ("ns").

3. The system of claim 1, wherein the laser beam has a pulse energy from 100 to 2500 millijoules ("mj").

4. The system of claim 1, wherein the laser beam has a spot size of from 1 to 15 millimeters.

5. The system of claim 1, wherein the laser beam has a fluence of 0.1 to 5 $j/cm^2$.

6. The system of claim 1, wherein the hydrogel patch is approximately 8 inches by 4 inches.

* * * * *